United States Patent [19]

Berninger et al.

[11] Patent Number: 5,194,370
[45] Date of Patent: Mar. 16, 1993

[54] PROMOTER LIGATION ACTIVATED TRANSCRIPTION AMPLIFICATION OF NUCLEIC ACID SEQUENCES

[75] Inventors: Mark S. Berninger, Gaithersburg; David M. Schuster, Poolesville; Ayoub Rashtchian, Gaithersburg, all of Md.

[73] Assignee: Life Technologies, Inc., Gaithersburg, Md.

[21] Appl. No.: 524,306

[22] Filed: May 16, 1990

[51] Int. Cl.$^5$ .................... C12Q 1/68; C12P 19/34; G01N 33/566; G01N 33/48
[52] U.S. Cl. .......................... 435/6; 435/91; 436/501; 436/94; 935/77; 935/78
[58] Field of Search ............. 435/6, 91, 193, 194, 435/199, 810; 935/77, 78; 436/501, 94

[56] References Cited

U.S. PATENT DOCUMENTS

| | | | |
|---|---|---|---|
| 4,800,159 | 6/1992 | Mullis et al. | 435/6 |
| 5,130,238 | 7/1992 | Malek et al. | 435/6 |

FOREIGN PATENT DOCUMENTS

| | | | |
|---|---|---|---|
| 0310229 | 5/1989 | European Pat. Off. | 435/91 |
| 0329822 | 8/1989 | European Pat. Off. | 435/91 |
| 0369775 | 5/1990 | European Pat. Off. | 435/91 |
| 8810315 | 12/1988 | PCT Int'l Appl. | 435/91 |

OTHER PUBLICATIONS

Kwoh et al., PNAS (U.S.A.) 86:1173-1177 (Feb., 1989).
Masukata et al., Cell 36: 513-522 (Feb., 1984).
Melton et al., Nuc. Acids Res. 12(18): 7035-7056 (1984).
Stoflet et al., Science 239: 491-494 (Jan. 29, 1988).
Krupp et al., Febs Letters 212(2): 271-275 (Feb. 1987).

*Primary Examiner*—Margaret Moskowitz
*Assistant Examiner*—Stephanie W. Zitomer
*Attorney, Agent, or Firm*—Sterne, Kessler, Goldstein & Fox

[57] ABSTRACT

This invention discloses a scheme for producing nucleic acid end products that are functionally or exactly identical to the starting products, thereby resulting in exponential amplification of a desired nucleic acid sequence. Specifically, sequences are cycled between RNA and DNA forms using the following basic steps: (1) a T7 RNA polymerase promoter is ligated onto a single-stranded DNA template; (2) T7 RNA polymerase makes many copies of RNA: (3) a complementary DNA is made from the RNA by extension of a primer by reverse transcriptase; and (4) the RNA template is removed by ribonuclease H. This amplification method is useful for purposes such as genetic research and diagnostic assays.

19 Claims, 4 Drawing Sheets

PROMOTER LIGATION ACTIVATED TRANSCRIPTION AMPLIFICATION OF NUCLEIC ACID SEQUENCES

FIELD OF THE INVENTION

The present invention is in the fields of molecular biology, genetic engineering, and medical or veterinary diagnostics, and more particularly relates to the amplification of nucleic acids.

BACKGROUND OF THE INVENTION

Amplification of nucleic acid sequences has become a very important technology in the biological sciences. The best known of these techniques is the polymerase chain reaction (PCR). This procedure amplifies specific nucleic acid sequences through a series of manipulations including denaturation, annealing of oligonucleotide primers, and extension of the primers with DNA polymerase (Mullis KB et al., U.S. Pat. Nos. 4,683,202, 4,683,195; Mullis K. B., EP 201,184; Erlich H., EP 50,424, EP 84,796, EP 258,017, EP 237,362; Erlich H., U.S. Pat. No. 4,582,788; Saiki R. et al., U.S. Pat. No. 4,683,202; Mullis K. B. et al. (1986) in Cold Spring Harbor Symp. Quant. Biol. 51:263; Saiki R. et al. (1985) Science 230:1350; Saiki R. et al. (1988) Science 231:487; Loh E. Y. et al. (1988) Science 243:217; etc.). (All references cited herein are hereby incorporated by reference.) These steps can be repeated many times, potentially resulting in large amplifications of the number of copies of the original specific sequence. It has been shown that even single molecules of DNA can be amplified to produce hundreds of nanograms of product (Li H. et al. (1988) Nature 335:414). Though PCR is widely used, it has several technical weaknesses, including need for a specialized piece of equipment and the amount of time needed to perform all of the cycles necessary to attain the desired level of amplification.

Other known nucleic acid amplification procedures include transcription-based amplification systems (Kwoh D. et al. (1989) Proc. Natl. Acad. Sci. USA 86:1173; Gingeras T. R. et al., PCT appl. WO 88/10315 (priority: U.S. patent application Ser. Nos. 064,141 and 202,978)). Schemes based on ligation of two (or more) oligonucleotides in the presence of nucleic acid having the sequence of the resulting "di-oligonucleotide", thereby amplifying the di-oligonucleotide, are also known (Wu D. Y. and Wallace R. B. (1989) Genomics 4:560).

Miller H. I. and Johnston S., PCT appl. WO 89/06700 (priority: U.S. patent application Ser. No. 146,462, filed Jan. 21, 1988), disclose a nucleic acid sequence amplification scheme based on the hybridization of a promoter/primer sequence to a target single-stranded DNA (ssDNA) followed by transcription of many RNA copies of the sequence. This scheme was not cyclic; i.e. new templates were not produced from the resultant RNA transcripts.

Davey C. and Malek L. T., EP 0,329,822, disclose a nucleic acid amplification process involving cyclically synthesizing single-stranded RNA (ssRNA), ssDNA, and double-stranded DNA (dsDNA). The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5'- to its homology to its template. This primer is then extended by DNA polymerase (exemplified by the large "Klenow" fragment of E. coli DNA polymerase I), resulting in a dsDNA molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

All of the above amplification procedures depend on the principle that an end product of a cycle is functionally identical to a starting material. Thus, by repeating cycles, the nucleic acid is amplified exponentially.

Methods that use thermo-cycling, e.g. PCR or Wu and Wallace, supra. have a theoretical maximum increase of product of 2-fold per cycle, because in each cycle a single product is made from each template. In practice, the exponent is always lower than 2. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

Methods that include a transcription step, e.g. that of the present invention or of Davey and Malek, supra. can increase product by more than a factor of 2 at each cycle. As 100 or more transcripts can be made from a single template, factors of 100 or more are theoretically readily attainable. Furthermore, if all steps are performed under identical conditions, no molecule finishing step need "wait" for any other before proceeding to the next step. Thus amplifications that are based on transcription and that do not require thermo-cycling are potentially much faster than thermo-cycling amplifications such as PCR.

SUMMARY OF THE INVENTION

It is an object of the present invention to provide an amplification scheme that has a high amplification factor. It is a further object of the present invention to provide an amplification scheme that can proceed without addition of components or change of conditions during each cycle, e.g that can be done isothermally in a sealed reaction volume.

To satisfy the above objects, the present invention provides such means for the amplification of a nucleic acid sequence. This invention provides a promoter ligation activated transcription ("LAT") of nucleic acid sequences. The invention is based on the principle of cycling between dsDNA and ssRNA. This cycling is done by installing an RNA polymerase promoter at one end of the nucleic acid sequence. This promoter is installed by ligating an oligonucleotide fragment that is double-stranded in nature to one end of the oligonucleotide molecule. By use of the present invention only one oligonucleotide primer need be provided.

DETAILED DESCRIPTION OF THE INVENTION

Figure 1:
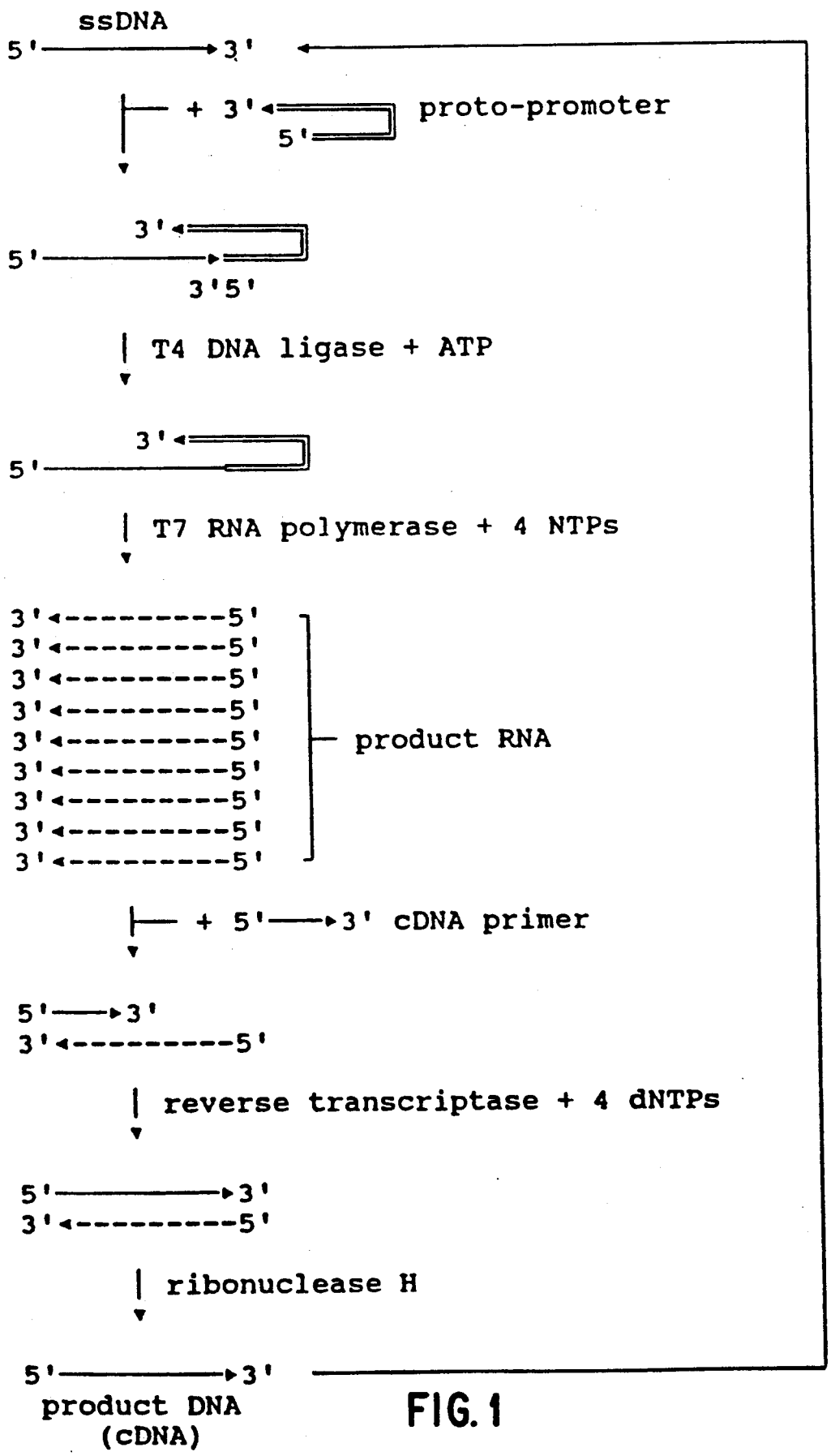
FIG. 1 presents the general scheme for the nucleic acid sequence amplification of the present invention. Solid lines represent DNA, the double line (—) representing a proto-promoter and the single lines (=) representing either DNA target, cDNA primer, or cDNA. Broken lines (---) represent RNA. An arrowhead (← or →) represents the 3'-end of a nucleic acid strand.

The present invention involves a method for producing nucleic acid sequence end products that are substantially identical to the starting products. To achieve this end, in the initial step nucleic acid sample sequences are tailored so that the 5'-end of the proto-promoter is adjacent to the 3'-end of the cDNA extension product extended from a primer (product DNA). More specifically, the present invention cycles sequences between RNA and DNA. (1) a RNA polymerase promoter is ligated onto a ssDNA template; (2) many copies of RNA are made; (3) a cDNA is made from the RNA by extension of a primer by reverse transcriptase; and (4) the RNA template is removed by RNase H. Then the cycle is repeated.

In more detail, the present invention is a method for amplifying or assaying a target nucleic acid sequence present, or possibly present, in a nucleic acid sample in a reaction volume under incubation conditions. This method involves performing a number steps cyclically. (For the purposes of explanation, one may arbitrarily start with any step.)

This method is performed by the following steps:
(a) annealing together a proto-promoter and a product DNA, thereby forming a product DNA/proto-promoter complex, wherein,
  (1) the proto-promoter has a single-stranded segment and a double-stranded segment,
  (2) the double-stranded segment of the proto-promoter encodes a promoter for a DNA-dependent RNA polymerase,
  (3) the single-stranded segment of the proto-promoter is complementary to the 3'-end of the product DNA,
  (4) the single-stranded segment of the proto-promoter is a 3'-overhang,
  (5) the single-stranded segment of the proto-promoter is capable of binding the proto-promoter to the product DNA in the reaction volume under the incubation conditions, and
  (6) the structure of the proto-promoter is such that the 5'-end of the double-stranded segment proximal to the single-stranded segment may be ligated by DNA ligase to the 3'-end of the product DNA in the reaction volume under the incubation conditions;
(b) ligating together the product DNA/proto-promoter complex, thereby forming a covalently-bound product DNA/proto-promoter combination, wherein
  (7) the orientation of the promoter is such that synthesized RNA contains a sequence identical to at least part of the single-stranded segment of the proto-promoter, and
  (8) the position of the promoter in the proto-promoter is such that when the proto-promoter is ligated to the 3'-end of the product DNA to form a product DNA/proto-promoter combination, the nucleotide formerly at the 3'-end of the product DNA may serve as template for the 5'-end of the product RNA;
(c) transcribing product DNA of the covalently-bound product DNA/proto-promoter combination with DNA-dependent RNA polymerase, thereby forming product RNA, wherein
  (9) the RNA polymerase is capable of synthesizing product RNA using the product DNA as a template in the reaction volume under the incubation conditions;
(d) annealing primer to product RNA, thereby forming a reverse transcription initiation complex, wherein
  (10) the primer must be complementary to the 3'-end of the product RNA, and
  (11) the primer is capable of priming the synthesis of product DNA from deoxyribonucleoside triphosphates using the product RNA as a template in the reaction volume under the incubation conditions;
(e) reverse transcribing product RNA with RNA-dependent DNA polymerase by extension of the primer of the reverse transcription initiation complex to form product DNA, thereby forming a product DNA:product RNA heteroduplex, wherein
  (12) the product DNA is comprised of
    (12a) at its 5'-end, the primer and
    (12b) at its 3'-end, an extension product synthesized by RNA-dependent DNA polymerase using product RNA as a template;
(f) releasing the DNA strand of the product DNA:product RNA heteroduplex, thereby liberating product DNA;
(g) repeating steps (a) through (f), thereby repeating a cycle, wherein
  (13) the product RNA and the product DNA are complementary to each other,
  (14) the product DNA is complementary to the target nucleic acid present, or possibly present, in the nucleic acid sample if the target nucleic acid is single-stranded RNA,
  (15) the product RNA is complementary to the target nucleic acid present, or possibly present, in the nucleic acid sample if the target nucleic acid is single-stranded DNA,
  (16) the product RNA is complementary to only one strand of the target nucleic acid present, or possibly present, in the nucleic acid sample if the target nucleic acid is double-stranded DNA, and
  (17) the product DNA is complementary to only one strand of the target nucleic acid present, or possibly present, in the nucleic acid sample if the target nucleic acid is double-stranded RNA,
  whereby in performing the above steps, target nucleic acid sequences that may be present in the reaction volume may be amplified in the form of product RNA and product DNA.

All of these steps may be performed simultaneously in a single reaction volume.

The present invention amplifies or assays a target nucleic acid sequence present, or possibly present, in a nucleic acid sample by means of several steps:
(a) first, a number of components are provided, including (1) the nucleic acid sample, (2) a primer, (3) a proto-promoter having a single-stranded segment and a double-stranded segment, (4) ribonucleotide triphosphates, (5) deoxyribonucleotide triphosphates, (6) RNA-dependent DNA polymerase, (7) ribonuclease H, (8) DNA ligase, (9) DNA-dependent RNA polymerase, and (10) buffer solution;
(b) combining together the components the components are combined together to form a reaction volume;
(c) incubating the reaction volume under conditions suitable for the amplification of target sequences that may be present in the nucleic acid sample, wherein
  (11) product RNA and product DNA are complementary to each other,
  (12) the product DNA is complementary to the target nucleic acid present, or possibly present, in the nucleic acid sample if the target nucleic acid is naturally single-stranded RNA,
  (13) the product RNA is complementary to the target nucleic acid present, or possibly present, in the nucleic acid sample if the target nucleic acid is naturally single-stranded DNA,
  (14) the product RNA is complementary to only one strand of the of the target nucleic acid present, or possibly present, in the nucleic acid sample if the target nucleic acid is naturally double-stranded DNA,
  (15) the product DNA is complementary to the target nucleic acid present, or possibly present, in the nucleic acid sample if the target nucleic acid is naturally single-stranded RNA,
  (16) the primer is complementary to the 3'-end of the product RNA,
  (17) the primer is capable of priming the synthesis of a product DNA from deoxyribonucleoside triphosphates using the product RNA as a template in the reaction volume under the incubation conditions,
  (18) the enzyme capable of releasing single-stranded DNA from RNA:DNA heteroduplexes is capable of releasing RNA that is in product RNA:product DNA heteroduplexes in the reaction volume under the reaction conditions, for example, RNase H degrades RNA that is in product RNA:product DNA heteroduplexes in the reaction volume under the reaction conditions,
  (19) the double-stranded segment of the proto-promoter encodes a promoter for the RNA polymerase,
  (20) the single-stranded segment of the proto-promoter is complementary to the 3'-end of the product DNA,
  (21) the single-stranded segment of the proto-promoter is a 3'-overhang,
  (22) the single-stranded segment of the proto-promoter is capable of binding the proto-promoter to the product DNA in the reaction volume under the incubation conditions,
  (23) the structure of the proto-promoter is such that the 5'-end of the double-stranded segment proximal to the single-stranded segment may be ligated by the DNA ligase to the 3'-end of the product DNA in the reaction volume under the incubation conditions,
  (24) the orientation of the promoter is such that synthesized RNA contains a sequence identical to at least part of the single-stranded segment of the proto-promoter,
  (25) the position of the promoter in the proto-promoter is such that when the proto-promoter is ligated to the 3'-end of the product DNA to form a product DNA/proto-promoter combination, the nucleotide formerly at the 3'-end of the product DNA may serve as template for the 5'-end of the product RNA,
  (26) the RNA polymerase is capable of synthesizing product RNA from the ribonucleoside triphosphates using the product DNA as a template in the reaction volume under the incubation conditions,
  (27) the bases of ribonucleoside triphosphates and deoxyribonucleoside triphosphates are sufficient to encode the product RNA and the product DNA, and
  (28) the components are present in such concentrations that the target nucleic acid sequences may be amplified in the reaction volume under the incubation conditions.

When all of these components are provided and the conditions are satisfied, target nucleic acid sequences that may be present in the reaction volume may be amplified to form product DNA and product RNA.

Another embodiment of this invention are kits for amplifying or assaying in a reaction volume under conditions suitable for the amplification of target nucleic acid sequences that may be present in a nucleic acid sample. A kit includes (1) a primer, (2) a proto-promoter comprising (2a) a single-stranded segment and (2b) a double-stranded segment, (3) ribonucleotidetriphosphates, (4) deoxyribonucleotide triphosphates, (5) RNA-dependent DNA polymerase, (6) an enzyme capable of releasing single-stranded DNA from RNA:DNA heteroduplexes, (7) DNA ligase, (8) DNA-dependent RNA polymerase, and (9) buffer solution, wherein
  (10) product RNA and product DNA are complementary to each other,
  (11) the product DNA is complementary to the target nucleic acid present, or possibly present, in the nucleic acid sample if the target nucleic acid is single-stranded RNA,
  (12) the product RNA is complementary to the target nucleic acid present, or possibly present, in the nucleic acid sample if the target nucleic acid is single-stranded DNA,
  (13) the product RNA is complementary to only one strand of the of the target nucleic acid present, or possibly present, in the nucleic acid sample if the target nucleic acid is double-stranded DNA,
  (14) the product DNA is complementary to only one strand of the of the target nucleic acid present, or possibly present, in the nucleic acid sample if the target nucleic acid is double-stranded RNA,
  (15) the primer is complementary to the 3'-end of the product RNA,
  (16) the primer is capable of priming the synthesis of product DNA from deoxyribonucleoside triphosphates using the product RNA as a template in the reaction volume under the incubation conditions,
  (17) the enzyme capable of releasing single-stranded DNA from RNA:DNA heteroduplexes is capable of releasing RNA that is in product RNA:product DNA heteroduplexes in the reaction volume under the reaction conditions,

(18) the double-stranded segment of the proto-promoter encodes a promoter for the RNA polymerase,

(19) the single-stranded segment of the proto-promoter is complementary to the 3'-end of the product DNA,

(20) the single-stranded segment of the proto-promoter is a 3'-overhang,

(21) the single-stranded segment of the proto-promoter is capable of binding the proto-promoter to the product DNA in the reaction volume under the incubation conditions,

(22) the structure of the proto-promoter is such that the 5'-end of the double-stranded segment proximal to the single-stranded segment may be ligated by the DNA ligase to the 3'-end of the product DNA in the reaction volume under the incubation conditions,

(23) the orientation of the promoter is such that synthesized RNA contains a sequence identical to at least part of the single-stranded segment of the proto-promoter,

(24) the position of the promoter in the proto-promoter is such that when the proto-promoter is ligated to the 3'-end of the product DNA to form a product DNA/proto-promoter combination, the nucleotide formerly at the 3'-end of the product DNA may serve as template for the 5'-end of the product RNA,

(25) the RNA polymerase is capable of synthesizing product RNA from the ribonucleoside triphosphates using the product DNA as a template in the reaction volume under the incubation conditions,

(26) the bases of ribonucleoside triphosphates and deoxyribonucleoside triphosphates provided in step (a) are sufficient to encode the product RNA and the product DNA, and

(27) the components are present in such concentrations that the product nucleic acid sequences may be amplified in the reaction volume under the incubation conditions;

whereby target nucleic acid sequences that may be present in the reaction volume may be amplified by the kit in the form of product RNA and product DNA.

Preferably the primer is at least 8 nucleotides long to assure good priming. Preferably, the single-stranded segment of the proto-promoter is also at least 8 nucleotides long. However, the single-stranded segment of the proto-promoter may be 4 nucleotides long, e.g. the result of a restriction endonuclease digestion, or, as a special case, 0 (zero) nucleotides long. In this latter case, the proto-promoter is blunt-end ligated onto the target, an operation well known to the art. As exemplified herein, the double-stranded segment of the proto-promoter is at least 22 nucleotides pairs long, i.e. the length of a T7 promoter. In some embodiments the 3'-end of the single-stranded segment of the proto-promoter is incapable of serving as a primer for extension by the RNA-dependent DNA polymerase, for example, by being "blocked" by a cordycepin residue at its 3'-end. It is possible that the two strands of the double-stranded segment of the proto-promoter may not be covalently linked. In this case, the double-stranded segment may be formed of two complementary oligonucleotides or may be two regions of a single oligonucleotide connected by a single-stranded linker.

Preferably, the RNA-dependent DNA polymerase is avian myeloma virus reverse transcriptase or Moloney murine leukemia virus reverse transcriptase; the ribonuclease H is *E. coli* ribonuclease H; the DNA ligase is T4 DNA ligase; and, the DNA-dependent RNA polymerase is T7 DNA polymerase.

In another embodiment, a helicase may be substituted for or used in conjunction with RNase H as a means of separating the RNA and DNA strands of RNA:DNA heteroduplexes. In this embodiment, the RNA strand of the heteroduplex may not be degraded, but may be recycled to serve again as a template for reverse transcription. In these embodiments the DNA strand of the duplex is made available for binding by and ligation to proto-promoter and subsequent transcription.

In the following explanation, a cyclic process is being described. Though a cycle may have an entry point or exit point, it does not have a beginning or end. Therefore, the starting point for a description is arbitrary. The present version will start with a single-stranded RNA (ssRNA) having both its 3'-end and its 5'-end at defined locations in a possibly larger sequence. FIG. 1 is a diagrammatic representation of this scheme.

During the nucleic acid sequence amplification of the present invention, the nucleic acid sequence being amplified alternates between RNA and DNA. Each of the two complementary strands is amplified either as RNA or DNA, but not both. For example, if one amplified a sequence containing, in double-stranded form, the sequence $$5'\ldots dAdAdAdCdG \ldots 3'$$

$$3'\ldots dTdTdTdGdC \ldots 5'$$

the amplification might contain $$5'\ldots rArArArCrG \ldots 3' \text{ and } 3'\ldots dTdTdTdGdC \ldots 5' \quad (1)$$

or $$5'\ldots dAdAdAdCdG \ldots 3' \text{ and } 3'\ldots rTrTrTrGrC \ldots 5' \quad (2)$$

but not both (1) and (2). In cases where the target starts as dsDNA, either the former or latter situation may be used.

In one embodiment of the present invention, an RNA having a unique 5'-end is the target which one either amplifies or, in an assay for the absence of this target, attempts to amplify. First, a DNA oligonucleotide primer is hybridized to the RNA. The primer must have a free 3'-hydroxyl and preferably has a free 5'-hydroxyl. The RNA serves as a template. The primer is extended with reverse transcriptase (RT) to make a full length cDNA (copy DNA or complementary DNA) of the RNA template, thereby forming a RNA:DNA duplex. Optionally, this primer may be chosen to be near the 5'-end of the template so that chain extension can be short. Second, the RNA is digested by RNase H to provide a single-stranded cDNA for the next step. Third, a DNA is hybridized and ligated to the 3'-end of the cDNA. This DNA is referred to as a "proto-promoter" because it carries an RNA polymerase promoter, preferably that for T7 RNA polymerase, in a double-stranded segment. This DNA also has a single-stranded segment 3'-form (i.e. downstream from) the promoter. This single-stranded DNA terminates in a 3'-end, i.e. is a 3'-overhang, and is complementary to a portion of the target. The overhang may optionally have a 2',3'-dideoxy end so that it cannot be extended by a DNA polymerase. The single-stranded portion of the proto-promoter is responsible for the annealing of the proto-promoter DNA to the single-stranded DNA produced by reverse transcriptase. The binding and ligation the proto-promoter to the ssDNA is what necessitates that the ssRNA "starting" material in the "first" step have a defined 5'-end; the end of the ssDNA must abut the 5'-end of the proto-promoter at the start of the dsDNA portion of the proto-promoter for ligation to occur. Fourth, RNA is synthesized from the promoter-carrying DNA by an appropriate RNA polymerase, preferably that of E. coli bacteriophage T7. This RNA is the starting point for a repeat of this process, starting at the first step, thereby closing, but not completing, the cycle.

This general cycle may be entered with an RNA molecule as the target. The target RNA need not have a defined 3'-end. The process proceeds as described above without modification even if the 3'-end extends beyond the point that the primer anneals. Since the DNA strand that serves as a transcriptional template does not extend beyond (i.e. 5'-from) the sequence, it will not be transcribed. Sequences beyond the location of the primer are never amplified.

In some embodiments, the target RNA molecules in a sample may not have unique 5'-ends. In these embodiments, a means to generate a defined 5'-end in the initial stages of a reaction is provided. One possible means involves use of a DNA oligonucleotide having a double-stranded segment that contains a FokI site and a single-stranded segment that binds to the target sequence after it has been converted to DNA form. As is well known in the art, this type of oligonucleotide can be used with the restriction enzyme FokI to cut a single-stranded DNA at almost any desired sequence (Szybalski W. (1985) Gene 40:169; Podhajska A. J. and Szybalski W. (1985) Gene 40:175). Alternatively, a linear DNA oligonucleotide can be annealed to the target at a location that encodes a recognition site of a restriction enzyme that can cut RNA:DNA heteroduplexes. Cutting the target RNA:oligodeoxyribonucleotide combination with the enzyme will then generate a defined end. Other means to generate a defined end may be adapted for use as part of this invention.

In another embodiment of the present invention, a DNA is the target which either one amplifies or, in an assay for the absence of this target, attempts to amplify. The DNA must have a defined end at the site at which the proto-promoter is annealed. The defined end is most conveniently generated by digestion with a restriction endonuclease. The enzyme is chosen that does not cut within the DNA segment one wishes to amplify, i.e. there is a site where the proto-promoter binds to the target but not between that point and the location of primer binding. The resulting digestion products are then denatured. The denatured DNA is then mixed with the desired primer, proto-promoter, and other amplification components, and an amplification is performed.

As an alternative method of introducing a defined end into a DNA, a presumptive target DNA is first denatured and hybridized to a primer oligonucleotide and to an oligonucleotide which generates a restriction site; the latter is designated herein the "cutter". The restriction site of the cutter must be unique within all of the sequence involved in the amplification. The primer and the cutter are designed to bind to the same strand of the target and such that the cutter is 3'-from the primer. The 5'-end of the cutter, i.e. the portion proximal to the primer, preferably extends only a few bases past the restriction site, thereby making the truncated oligonucleotide resulting from restriction endonuclease cleavage unstably bound to the target. The primer may optionally be tethered to a solid support, e.g. a bead, to provide for capture of the target DNA from the sample. The cutter oligonucleotide may optionally have a 2',3'-dideoxy end so that it cannot be extended by a DNA polymerase. Second, a cDNA is the synthesized by DNA polymerase using the target RNA as a template and the primer oligonucleotide as a primer. Third, the resulting target DNA/cDNA a DNA is hybridized and ligated to the 3'-end of the proto-promoter. This DNA carries an RNA polymerase promoter, preferably that for T7 RNA polymerase, in a double-stranded segment. This DNA also has a single-stranded segment 3'-from (i.e. downstream from) the promoter. This single-stranded DNA terminates in a 3'-end, i.e. is a 3'-overhang, and is complementary to a portion of the target. The overhang may optionally have a 2',3'-dideoxy end so that it cannot be extended. This DNA is ligated to yield a continuous double-stranded DNA template for T7 RNA polymerase. Transcription with the appropriate RNA polymerase, preferably that of T7, then produces an RNA which can serve to initiate the cyclic reaction described above for amplification of an RNA having a defined 5'-end.

Note that if a target DNA, or the cDNA made from a target RNA, is not long enough to be bound to the single-stranded segment of the proto-promoter and not long enough to abut the proto-promoter and be ligated thereto, the target DNA or cDNA can be extended by reverse transcriptase using the single-stranded segment as a template until the target DNA or cDNA is long enough to be ligated to the proto-promoter.

In the above scheme, amplified sequences do not solely come from the target; some derive from a component of the amplification scheme. In some uses of promoter ligation activated amplification one may wish that no sequences of the added components be present in the amplified products. To achieve this end, components that have restriction sites at their ends which abut the target sequences may be designed. In another embodiment, a promoter-bearing fragment that binds to the target by means of a restriction site "sticky-end" and which regenerates an intact restriction site may be designed. Thus, after an amplification by either scheme, the added sequences can be removed by cutting with a restriction endonuclease.

All of the enzymes used in this amplification reaction, reverse transcriptase, T7 RNA polymerase, RNase H, and T4 DNA ligase, may be active under the same reaction conditions. Indeed, buffers exist in which all enzymes are near their optimal reaction conditions. Therefore, the amplification process of the present invention can be done in a single reaction volume without any change of conditions such as addition of reactants or temperature cycling. Thus, though this process has several steps at a molecular level, operationally it may have a single step. Once the reactants are mixed together, one need not add anything or change conditions, e.g. temperature, until the amplification reaction has exhausted one or more components. During this time, the nucleic acid sequence being amplified will have been increased many-fold. The level of increase will be sufficient for many purposes; however, for some purposes the reaction may have to be repeated with fresh components to achieve the desired level of amplification.

When defining conditions to be used in any specific embodiment of the present invention, there are several possible problems that should be checked during assay validation. First, the primers can, in some cases, act as templates for T7 polymerase, albeit inefficiently, and produce RNA which could inhibit subsequent priming of RNA. To minimize the likelihood of this potential interfering reaction, primers should be chosen which cannot prime on the single-stranded portion of the proto-promoter. By measuring the addition of nucleotides by T7 RNA polymerase to the 3'-end of a candidate primer in the absence of other enzymes or DNA a candidate primer can be tested. Second, in the DNA amplification scheme, a sequence which comes exclusively from the target is all that is amplified: sequences in the primer and proto-promoter are also present in amplification products. One should verify that amplified sequences do, indeed, contain target sequences, and not just proto-promoter or primer sequences. Third, in the cycling reaction, the T7 promoter used to ligate to the cDNA could compete for binding to T7 RNA polymerase and significantly reduce amplification efficiency. This can be minimized with a titration of the quantities of enzyme and proto-promoter.

This invention may be combined with many other processes in the arts of molecular biology to achieve a specific end. Of particular interest is pre-purifying the target sequence from the other sequences in the nucleic acid sample. This can be accomplish most advantageously by annealing the nucleic acid sample to an oligonucleotide that is complementary to the target and is immobilized on a solid support. A convenient support would be a micro-bead, especially a magnetic micro-bead. After being so bound, the non-target sequences could be washed away, resulting in a complete or a partial purification.

After an amplification is performed, one may wish to detect any amplification products produced. Any number of techniques known to the art may be adapted to this end without undue experimentation. Particularly advantageous in some situations is the capture of RNA amplification products by a DNA oligonucleotide complementary to an RNA sequence determined by the target sequence, the oligonucleotide being bound to a solid support such as a magnetic micro-bead. Preferably, this oligonucleotide3 s sequence does not overlap with that of any oligonucleotide used to purify the target before the amplification. RNA:DNA hybrids thus formed may then be detected by antibodies that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Those in the art will find that the present invention can be adapted to incorporate many detection schemes.

EXAMPLES

Example 1

Materials and methods

Example 1.1

Materials

Enzymes used for the amplification procedure (T7 RNA polymerase, *E. coli* RNase H, Superscript ™ RNase H⁻ reverse transcriptase, T4 DNA ligase) and human placental ribonuclease inhibitor were obtained from Bethesda Research Laboratories. Deoxyribonucleoside triphosphates (dATP, dCTP, dGTP, and dTTP) and ribonucleoside triphosphates (ATP, CTP, GTP, and UTP) were purchased from Pharmacia as 100 Mm solutions.

Example 1.2

Preparation of cordycepin-CPG

To assure that the proto-promoter did not act as a primer, a cordycepin residue was desired at its 3'-end. A cordycepin modified CPG column was used to synthesize 3'-oligodeoxynucleotides. The CPG modification was made using standard protocols described by Atkinson T. and Smith M. (1984) in *Oligonucleotide Synthesis: A Practical Approach*, ed.: Gait M. J., IRL Press (Oxford, Washington DC), pp. 35-81, and Jones R. A. (1984) in Gait, supra. pp. 23-34.

Figure 2:
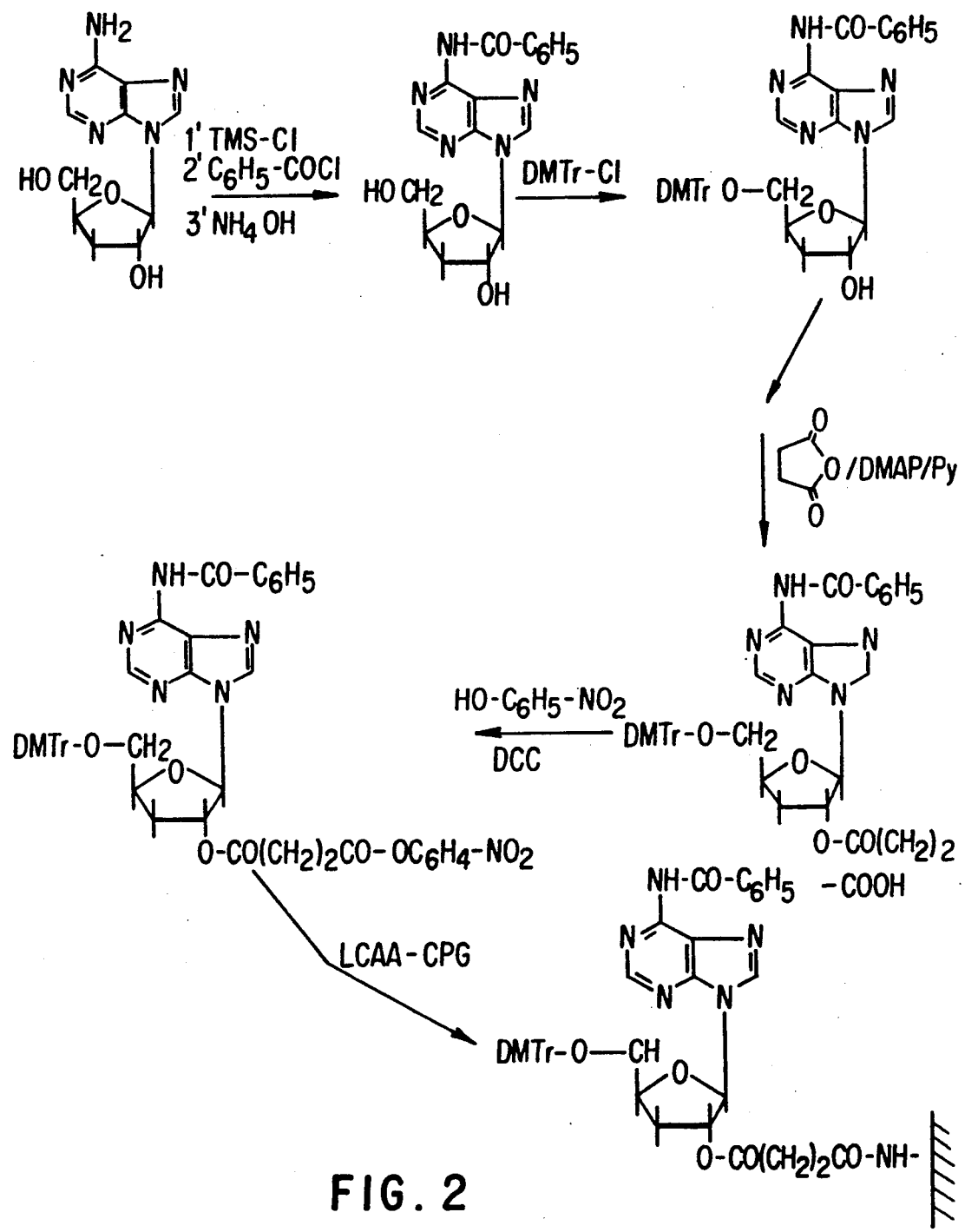
FIG. 2 diagrams the synthesis of cordycepin-CPG, which was used to synthesize proto-promoters.

FIG. 2 presents an out-line of this synthesis. Briefly, $N^6$-benzoylcordycepin was obtained by treating cordycepin with trimethylchlorosilane, benzoyl chloride and ammonium hydroxide sequentially. The $N^6$-benzoylcordycepin was crystallized from water, and converted to the 5'-dimethoxytrityl-$N^6$-benzoylcordycepin. The nucleoside was succinylated and conjugated to LCAA-CPG.

Example 1.3

Oligonucleotide synthesis

Oligonucleotides were synthesized by cyanoethyl-phosphoramidite chemistry using an Applied Biosystems 380A DNA synthesizer. Reagents used for syntheses were purchased from Cruachem. Oligonucleotides were purified by denaturing polyacrylamide gel electrophoresis. DNA was eluted from the gel matrix by crush and soak in 20 mM Tris-HCl (pH 8.0), 0.5M ammonium acetate, 1 mM EDTA, 0.01% sodium dodecyl sulfate at 37° C. for 16 hours, and then desalted by molecular exclusion chromatography using PD-10 columns from Pharmacia. Proto-promoter oligonucleotide was synthesized with a 3'-deoxyadenosine 5'-triphosphate residue at the 3'-terminus. The 5'-terminus of the proto-promoter was phosphorylated by the kinase reaction using the 5' DNA Terminus Labelling System from BRL according to the manufacturer's recommendations.

Example 1.4

Polyacrylamide gel electrophoresis

Samples (2.5 to 5 microl) were mixed with an equal volume of formamide dye mix (95% formamide, 25 mM EDTA, 0.01% xylene cyanol, 0.01% bromophenol blue), heat denatured for 2 to 3 minutes at 95° C., then placed on ice. Denatured sample (2.5 to 5 microl) was applied to a 0.4 mm thick 40 cm long 7M urea, 8% polyacrylamide sequencing gel and electrophoresed at 75 Watts constant power until the bromophenol blue dye had migrated approximately 30 cm. Gels were transferred to Whatmann 3MM paper, dried, and autoradiographed.

Example 2

"Dot" blot assays 5 microl of a 25 microl amplification reaction was placed in 5 microl 10 Tris·HCl, pH 8.1, 40 mM EDTA to stop the amplification reaction. 5 microl of the stopped reaction was then placed in 15 microl "glyoxal mix" (25% glyoxal, 50% DMSO, 10 mM sodium phosphate, pH 6.8) and heated for one hour at 50° C. 180 microl 6X SSC (SSC=standard saline citrate; 1X SSC=50 mM NaCl, 15 mM sodium citrate, pH 7.0) was then added to the glyoxylated amplification products. The resulting mixture, representing 10% of the original amplification products, was then applied to a nylon membrane (Amersham Hybond-NTM under partial vacuum (about 150 mm HG) in a Bio-Rad dot blot apparatus. The filter was then baked for 30 min. and the bound nucleic acid was cross-linked to the filter by ultraviolet trans-illumination for about 90 sec.

The filter was then pre-hybridized at 55° C. for about 1 hr in 4 ml/100 cm$^2$ filter of 5% SDS, 0.1% gelatin, 1 M NaCl, 50 mM sodium phosphate, pH 6.8, 1 mM Na$_2$EDTA, 30% formamide, and 15 microg/ml tRNA. 3–4×10$^6$ cpm of radioactively labelled probe was then added for each ml of hybridization fluid and hybridized for 2–4 hr at 42° C. The filter was then washed once in 2X SSC at room temperature and then in 3 changes of 0.1X SSC at 42° C. The filter was then placed against X-ray film (Kodak X-OMAT) in a cassette and placed at −80° C. for autoradiography.

Example 3

Primer recruitment assay cDNA primer was end-labelled by the kinase reaction using [gamma-$^{32}$P] ATP (3000, Ci/mmol) from New England Nuclear, and the 5′ DNA Terminus Labelling System from Bethesda Research Laboratories according to the supplier3 s recommendations. Unincorporated radio-labelled nucleoside triphosphate was removed by gel filtration chromatography using a PD-10 column from Pharmacia. Primer concentration was adjusted to 2 pmol/microl with a specific activity of 650,000 dpm/pmol.

Reaction mixtures used to amplify target contained 50 mM Tris.HCl (experiment 1 at pH 8.1, experiment 2 at pH 8.3), 175 mM potassium glutamate, 6 mM MgCl$_2$, 8% polyethylene glycol 8000, 0.01% Triton X-100, 1 mM ATP, 1 mM CTP, 1 mM GTP, 1 mM UTP, 0.25 mM dATP, 0.25 mM dCTP, 0.25 mM dGTP, 0.25 mM dTTP, 10 mM dithiothreitol, 2 pmoles Proto-promoter, 4 pmole $^{32}$P end-labelled cDNA primer,-20 units Superscript TM Reverse Transcriptase (BRL), 400 units T7 RNA polymerase, 1 unit T4 DNA ligase, RNase H (exp. 1: 0.2 units; exp. 2: 0.05 units) in a 25 microl volume. Target sequence (63-mer oligonucleotide) was varied from 0 to 100 attomoles. Control reactions included omission of either proto-promoter, target, ligase, or RNase H. Reactions were incubated at 42° C. Aliquots (5 microl) from each reaction were removed at various times and mixed with 5 microl of formamide dye mix. 2.5 microl of each reaction time point was electrophoresed on a 0.4 mm 7M urea, 8% polyacrylamide sequencing gel as described above. The incorporation of the $^{32}$P end-labelled cDNA primer into cDNA product and cDNA/proto-promoter ligation product was assessed from the gel autoradiograph. The autoradiograph was over-exposed to make trace bands more easily visible.

Example 4

Oligonucleotide sequences—experiment 1

Figure 3:
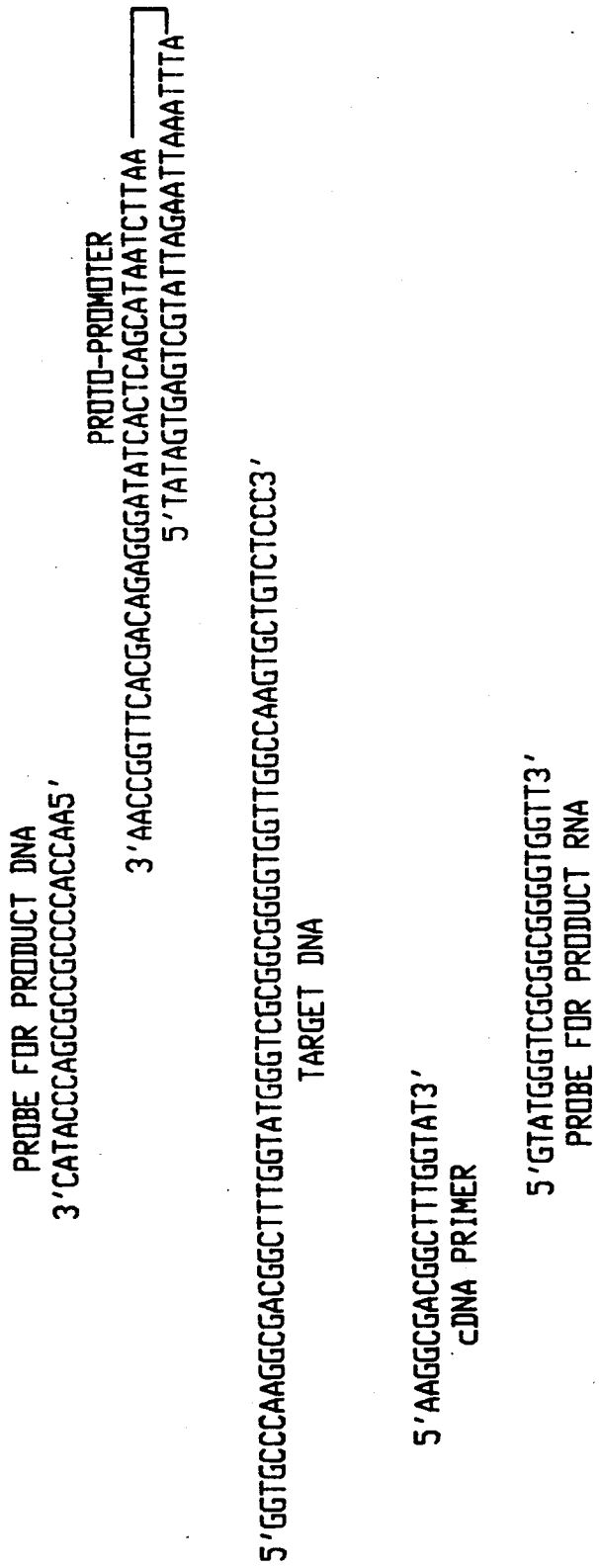
FIG. 3 presents the sequences, structures, and relationships of oligonucleotides used in the Examples 4, 5, and 6.

Sequences and secondary structures of oligonucleotides in this amplification are presented below. Their relationships are diagrammed in FIG. 3.

The 19-mer cDNA primer had the following sequence:

5'AAGGCGACGGCTTTGGTAT3'

The oligonucleotide probe used to detect amplified target RNA sequences had the following sequence:

5'GTATGGGTCGCGGCGGGGTGGTT3'

The oligonucleotide probe used to detect amplified target DNA sequences had the following sequence:

5'AACCACCCCGCCGCGACCCATAC3'

These two 23-mer oligonucleotide probes are exactly complementary to each other.

The 71-mer proto-promoter had the following sequence:

5' <u>TATAGTGAGTCGTATTAGAATT</u>aaattta<u>AATTCTAATACGACTCACTATA</u>gggagacagcacttggccaa3'

The two underlined 22 nucleotide segments are complementary to each other and encode a T7 DNA-dependent RNA polymerase promoter, the sequence indicated by lower case in the middle is a 7 nucleotide single-stranded loop connecting the two strands of the promoter, and the sequence indicated by lower case at the 3′-end is a 20 nucleotide single-stranded segment complementary to the 3′-end of the target. Note that the final adenosine at the 3′ end is cordycepin.

The 63-mer target DNA had the following sequence:

5'GGTGCCC<u>AAGGCGACGGCTTTG</u>gtatgggtcgcggcggggtggtt<u>GGCCAAGTGCTGTCTCCC</u>3'

The 5′-underlined segment is identical to the sequence of the cDNA primer, the 3′-underlined segment is complementary to the single-stranded segment of the proto-promoter, and the segment given in lower case is identical to the sequence of the oligonucleotide probe used to detect amplified RNA target sequences and complementary to the oligonucleotide probe used to detect amplified DNA target sequences.

Example 5

Results of the primer recruitment experiment

Polyacrylamide gel electrophoresis of the reaction products made in Example 2 showed a conversion of the radio-labeled 19-mer primer to a 54-mer product (primer/cDNA extension product combination) and a 125-mer which results from ligation of the 54-mer and the 71-mer proto-promoter.

Control reactions performed for 2 hr. and lacking target DNA failed to show any detectable 54-mer or 125-mer products; 3 hr. reactions showed very faint bands, estimated to be much less than 1% of the radioactivity in the amplified products, migrating at these molecular weights. These bands are thought to result from amplification of contaminating target molecules. Other bands were observed on the gels at lengths that do not easily suggest an explanation for their presence.

Control reactions lacking proto-promoter did not result in conversion of 19-mer primer to higher molecular weight product.

Control reactions lacking RNase H showed a barely visible 54-mer primer/cDNA extension product which results from simple transcription of target DNA which has ligated to proto-promoter and its subsequent reverse transcription. This product is the result of a linear process, as contrasted with the exponential process of the present invention. The 125-mer ligation product was not observed.

Control reactions lacking ligase had a substantial amount of 54-mer cDNA product only after 3 hr. incubation while no 125-mer was visible. A heterogeneous group of bands was present, ranging in size from about 54-mers to about 85-mers, were observed. These bands are believed to result from extension of cDNA product by reverse transcriptase which uses the proto-promoter as template through a strand displacement mechanism. This side reaction appears to be an exponential in nature.

In other experiments, omission of T7 RNA polymerase or reverse transcriptase did not result in conversion of 19-mer primer to higher molecular weight product.

Example 6

Results of a dot blot experiment

Quantitative dot blots hybridization assays were performed in order to assess the level of amplification achieved by the method of this invention. Amplification reactions were done generally as described for the primer recruitment assay (Example 2). They differed in that primer used for cDNA synthesis was not radioactively labeled that buffer conditions were as described by Davey C. and Malek L. T., *Eur. Pat.* publ. 329,882, example 3, that enzyme levels were modified (1000 units T7 RNA polymerase, 28 units AMV reverse transcriptase (Seikagaku America Inc., Rockville MD.), 0.05 units RNase H, and 1 unit T4 DNA ligase), and that the reaction contained 20 units of human placental RNase inhibitor. Dot blots were performed in duplicate to analyze both RNA product and cDNA by hybridizing to probes specifically designed to hybridized to either transcribed RNA or reverse transcribed cDNA. Amplification products were compared to measured amounts of RNA or DNA, as appropriate.

When probing for RNA amplification products, after 2 hr. of amplification $5 \times 10^4$, $5 \times 10^5$, and $5 \times 10^6$ molecules of DNA were amplified about $3 \times 10^5$-fold, about $1 \times 10^5$-fold, and greater than $2 \times 10^4$-fold, respectively. The latter amplification, whose film exposure was over-exposed for the 2 hr. aliquot, was amplified about $1 \times 10^4$-fold at the end of one hour.

In controls lacking target, nucleotides, or a combination of ligase, proto-promoter, and RNase H, no amplification signal was observed. In separate controls which contained either no cDNA primer, no RNase H, no proto-promoter, or which lacked a combination of proto-promoter and ligase showed signals estimated to be less than or equal to about $1 \times 10^3$-fold amplification, and certainly less than $2 \times 10^3$-fold amplification. When ligase was omitted from a reaction, signal equivalent to less than $5 \times 10^4$-fold amplification was observed.

When probing for DNA amplification products, after 2 hr. of amplification $5 \times 10^4$, $5 \times 10^5$, and $5 \times 10^6$ molecules of DNA were amplified about $4 \times 10^5$-fold, about $2 \times 10^4$-fold, and about $2 \times 10^4$-fold, respectively. (Since the first and last value so closely match those found for amplification of RNA, the middle value may be incorrect, the correct value being higher.)

Control reactions lacking either target DNA, cDNA primer, proto-promoter, nucleotides, a combination of proto-promoter and ligase, or a combination of proto-promoter, ligase, and RNase H, showed no detectable amplification signal. The control reaction lacking RNase H showed a signal equivalent to an about $4 \times 10^3$-fold amplification while the control lacking ligase had a signal in the range of about $6 \times 10^3$-fold to about $1.5 \times 10^4$-fold.

Example 7

Oligonucleotide sequences—experiment 2

Figure 4:
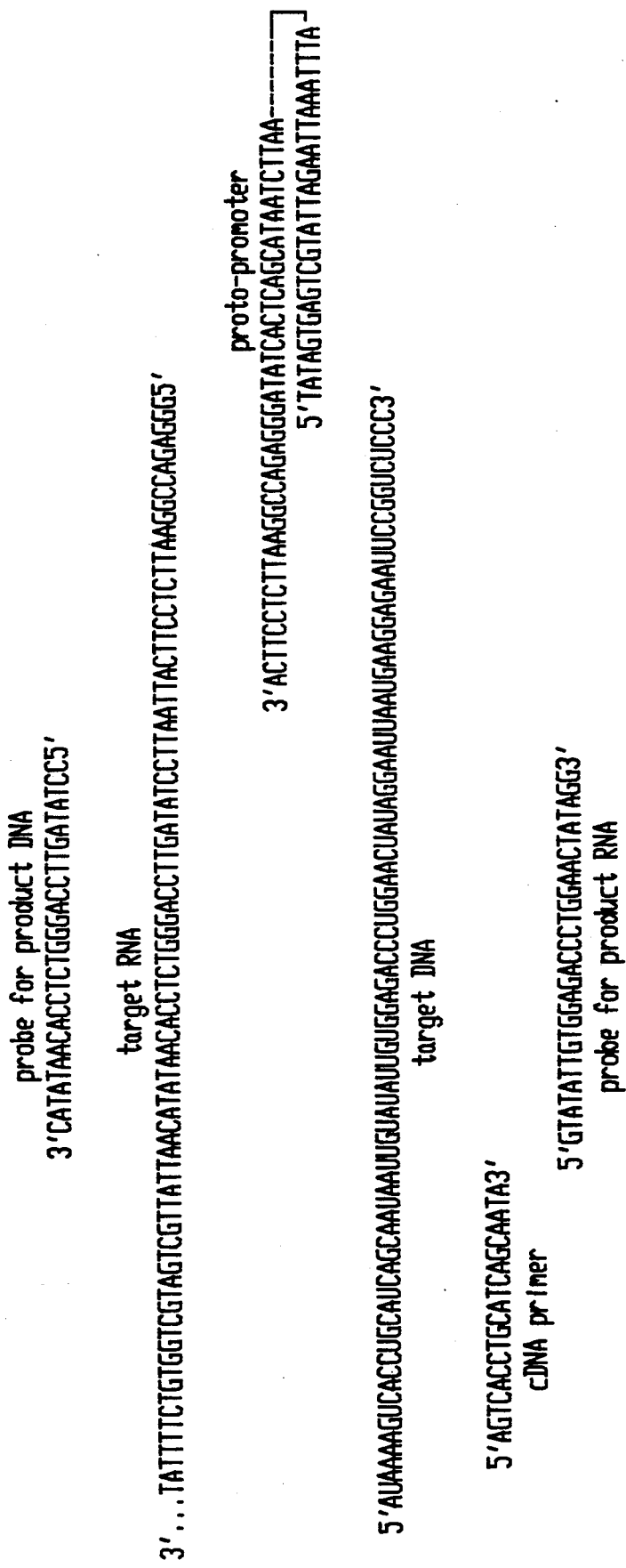
FIG. 4 presents the sequences, structures, and relationships of oligonucleotides used in the Examples 7 and 8.

Sequences and secondary structures of oligonucleotides used in this amplification are present below. Their relationships are diagrammed in FIG. 4.

The 20-mer cDNA primer had the following sequence:

5'AGTCACCTGCATCAGCAATA3'

The 29-mer oligonucleotide probe used to detect amplified target RNA sequences had the following sequence:

5'gtatattgtggAGACCCTGGAACTATAGG3'

The 40-mer oligonucleotide probe used to detect amplified target DNA sequences had the following sequence:

5'ccggaattctccttcattaattCCTATAGTT-
CCAGGGTCT3'

These two oligonucleotide probes are exactly complementary to each other in the region indicated by upper case letters.

The 72-mer proto-promoter had the following sequence:

5'TATAGTGAGTCGTATTAGAATTaaattaAATTCTAATACGACTCACTATAgggagaccggaattctccttca3'

The two underlined 22 nucleotide segments are complementary to each other and encode a T7 DNA-dependent RNA polymerase promoter, the sequence indicated by lower case in the middle is a 7 nucleotide single-stranded loop connecting the two strands of the promoter, and the sequence indicated by lower case at the 3'-end is a 21 nucleotide single-stranded segment complementary to the 3'-end of the target. Note that the final adenosine at the 3' end is cordycepin.

The 85-mer target DNA had the following sequence:

5'AUAAA<u>AGUCACCUGCAUCAGCAAUA</u>AUUguauauuuguggagacccuggaacuauaggAAUUAA<u>UGAAGGAGAAUUCCGGUCUCCC</u>3'

Note that this oligonucleotide used deoxyuridine instead of deoxythymidine. The 5'-underlined segment is identical to the sequence of the cDNA primer, the 3'-underlined segment is complementary to the single-stranded segment of the proto-promoter, and the segment given in lower case is identical to the sequence of the oligonucleotide probe used to detect amplified RNA target sequences and complementary to the oligonucleotide probe used to detect amplified DNA target sequences.

The 5'-end of 668 bp target RNA was an in vitro transcript of human papillomavirus type 16 open reading frame L1 (Seedorf K. et al. (1985) Virol. 145:181–185). The reverse complement of the 85-mer DNA target was totally contained within the RNA target, and the reverse complement and the 5'-end RNA target were identical in sequence to each other. In other words, the 5'-end of the target DNA and the 3'-end of the target DNA oligonucleotide were exactly the complementary to each other.

Example 8

Results of a dot blot experiment

Quantitative dot blots hybridization assays were performed in order to assess the level of amplification achieved by the method of this invention. Amplification was done as described for the primer recruitment assay (Example 2) except that primer used for cDNA synthesis was not radioactively labeled. Dot blots were performed in duplicate to analyze of both RNA product and cDNA by hybridizing to probes specifically designed to hybridized to either transcribed RNA or reverse transcribed cDNA. Amplification products were compared to measured amounts of RNA or DNA, as appropriate.

When probing for RNA amplification products, after 2 hr. of amplification, $1 \times 10^3$, $1 \times 10^4$, and $1 \times 10^5$ molecules of DNA target were amplified about $10^8$-fold, about $2 \times 10^7$-fold, and about $1.5 \times 10^6$-fold. No signals were detected from reactions containing no target or $1 \times 10^2$ molecules of target DNA.

When probing for RNA amplification products, after 2 hr. of amplification, $1 \times 10^5$ molecules of RNA target were amplified about $10^4$-fold. No signals were detected from reactions containing no target or $1 \times 10^2$, $1 \times 10^3$, or $1 \times 10^4$ molecules of target RNA.

When probing for DNA amplification products, after 2 hr. of amplification, $1 \times 10^3$, $1 \times 10^4$, and $1 \times 10^5$ molecules of DNA target were amplified about $10^7$-fold, about $5 \times 10^6$-fold, and about $10^6$-fold. No signals were detected from reactions containing no target or $1 \times 10^2$ molecules of target DNA.

When probing for DNA amplification products, after 2 hr. of amplification, no target, $1 \times 10^2$, $1 \times 10^3$, $1 \times 10^4$, and $1 \times 10^5$ molecules of RNA target, no signals were detected.

For amplifications containing $10^5$ molecules of either RNA target or DNA target, control reactions which lacked all enzymes, RNase H, or T4 DNA ligase showed no detectable amplification signal when probing for either RNA or DNA amplification products.

Southern blot analysis of DNA amplification products showed bands at the positions expected for a 78-mer product (primer/cDNA extension product combination) and a 151-mer resulting from ligation of the 78-mer and the 73-mer proto-promoter. Comparison of band intensity levels with standards gave amplification levels about the same as observed with the dot blot assay. Nothing was observed in lanes containing control reactions.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method for amplifying and detecting a target DNA sequence present, or possibly present, in a nucleic acid sample in a reaction volume under incubation conditions, comprising:
   (a) adding under hybridizing conditions to said sample the following components:
      (1) a primer,
      (2) a proto-promoter comprising
         (a) a double-stranded segment which encodes a promoter for a DNA dependent RNA polymerase, and
         (b) a single-stranded segment which is complementary to the 3' end of the target DNA and which is a 3' overhand;
      (3) ribonucleotide triphosphates,
      (4) deoxyribonucleotide triphosphates,
      (5) RNA-dependent DNA polymerase,
      (6) an enzyme capable of releasing single-stranded DNA from RNA-DNA heteroduplexes,
      (7) DNA ligase,
      (8) DNA-dependent RNA polymerase, and
      (9) buffer solution;
   (b) annealing together said proto-promoter and target DNA, thereby forming a target DNA/proto-promoter complex;
   (c) ligating together the target DNA/photo-promoter complex, thereby forming a covalently-bound target DNA/proto-promoter combination;
   (d) transcribing the covalently-bound target DNA/-proto-promoter combination with DNA-dependent RNA polymerase, thereby forming transcribed RNA;
   (e) annealing the primer to the transcribed RNA, thereby forming a reverse transcription initiation complex;
   (f) reverse transcribing the RNA with RNA-dependent DNA polymerase by extension of the primer of the reverse transcription initiation complex to form additional DNA, thereby forming a DNA-RNA heteroduplex;
   (g) releasing the DNA strand of the DNA-RNA heteroduplex, thereby liberating the additional DNA;

(h) repeating step (b) through (g), thereby providing a cyclical process; and (i) detecting nucleic acids synthesized from said cyclical process steps (b) through (h);

wherein said steps (b) through (h) are carried out without temperature cycling.

2. A method for amplifying and detecting a target RNA sequence present, or possibly present, in a nucleic acid sample in a reaction volume under incubation conditions, comprising:

(a) adding under hybridizing conditions to said sample the following components:
  (1) a primer,
  (2) a proto-promoter comprising
    (a) a double-stranded segment which encodes a promoter for a DNA dependent RNA polymerase, and
    (b) a single-stranded segment which is complementary to the 3' end of copy DNA reverse transcribed from target RNA and which is a 3' overhang;
  (3) ribonucleotide triphosphates,
  (4) deoxyribonucleotide triphosphates,
  (5) RNA-dependent DNA polymerase,
  (6) an enzyme capable of releasing single-stranded DNA from RNA-DNA heteroduplexes,
  (7) DNA ligase,
  (8) DNA-dependent RNA polymerase, and
  (9) buffer solution;

(b) annealing the primer to target RNA, thereby forming a first transcription initiation complex;

(c) reverse transcribing target RNA with RNA-dependent DNA polymerase by extension of the primer of the reverse transcription initiation complex to form copy DNA, thereby forming a DNA-RNA heteroduplex;

(d) releasing the DNA strand of the DNA-RNA heteroduplex, thereby liberating copy DNA;

(e) annealing together said proto-promoter and the copy DNA, thereby forming a copy DNA/proto-promoter complex;

(f) ligating together the copy DNA/proto-promoter complex, thereby forming a covalently bound copy DNA/proto-promoter combination;

(g) transcribing the covalently bound copy DNA/proto-promoter combination with DNA-dependent RNA polymerase, thereby forming additional RNA;

(h) repeating steps (b) through (g), thereby providing a cyclical process; and (i) detecting nucleic acids synthesized from said cyclical process steps (b) through (h);

wherein said steps (b) through (h) are carried out without temperature cycling.

3. A method as in claim 1, wherein the releasing of step (g) is digesting the DNA-RNA heteroduplex with ribonuclease H, thereby degrading the RNA of the DNA-RNA heteroduplex and liberating copy DNA.

4. A method as in claim 1, wherein the releasing step (g) is helix unwinding of the DNA-RNA heteroduplex with helicase, thereby denaturing the DNA-RNA heteroduplex and liberating copy DNA.

5. A methods as in claim 2, wherein the releasing step (d) is digesting the DNA-RNA heteroduplex with ribonuclease H, thereby degrading the RNA of the DNA-RNA heteroduplex and liberating copy DNA.

6. A method as in claim 2, wherein the releasing step (d) is helix unwinding of the DNA-RNA heteroduplex with helicase, thereby denaturing the DNA-RNA heteroduplex and liberating copy DNA.

7. A method as in claim 3 or 5, wherein the ribonuclease H is *E. coli* ribonuclease H.

8. A method as in claim 1, wherein the target nucleic acid is single-stranded DNA.

9. A method as in claim 1, wherein the target nucleic acid is double-stranded DNA.

10. A method as in claims 1 or 2, wherein the primer is at least 8 nucleotides long.

11. A method as in claims 1 or 2, wherein the single-stranded segment of the proto-promoter is at least 4 nucleotides long.

12. A method as in claims 1 or 2, wherein the single-stranded segment of the proto-promoter is at least 8 nucleotides long.

13. A method as in claims 1 or 2, wherein the double-stranded segment of the proto-promoter is at least 22 nucleotide pairs long.

14. A method as in claims 1 or 2, wherein the RNA-dependent DNA polymerase is avian myeloma virus reverse transcriptase.

15. A method as in claims 1 or 2, wherein the RNA-dependent DNA polymerase is Moloney murine leukemia virus reverse transcriptase.

16. A method as in claim 1 or 2, wherein the DNA ligase is T4 DNA ligase.

17. A method as in claims 1 or 2, wherein the DNA-dependent RNA polymerase is T7 DNA polymerase.

18. A method as in claims 1 or 2, wherein 3'-end of the single-stranded segment of the proto-promoter is incapable of serving as a primer for extension by the RNA-dependent DNA polymerase.

19. A method as in claims 1 or 2, wherein 3'-end of the single-stranded segment of the proto-promoter is a cordycepin residue.

* * * * *